United States Patent
Burek et al.

[11] Patent Number: 5,997,486
[45] Date of Patent: Dec. 7, 1999

[54] DEVICE FOR PARACENTISIS AND THORACENTISIS

[75] Inventors: Paul Burek, Aurora; Bonnie B. Vivian, Evergreen; David Skinkle, Denver, all of Colo.

[73] Assignee: Denver Biomaterials, Inc., Golden, Colo.

[21] Appl. No.: 09/066,236

[22] Filed: Apr. 24, 1998

[51] Int. Cl.[6] .................................................. A61B 5/00
[52] U.S. Cl. ........................... 600/573; 604/110; 604/158
[58] Field of Search ........................... 600/573, 576, 600/577, 579; 604/167, 169, 170, 158, 162, 164, 181, 110

[56] References Cited

U.S. PATENT DOCUMENTS

5,092,857  3/1992  Fleischhacker ........................ 604/167
5,334,159  8/1994  Turkel ........................ 604/158
5,657,963  8/1997  Hinchliffe et al. ........................ 604/167

*Primary Examiner*—Cary O'Connor
*Assistant Examiner*—Pamela L. Wingood
*Attorney, Agent, or Firm*—Gibson, Dunn & Crutcher LLP

[57] ABSTRACT

Apparatus for removing fluid from the body of a patient, such as in paracentesis and thoracentesis. Fluid may be withdrawn via a retractable needle assembly, including a sharp introducing needle and a retractile blunt needle. The needle assembly is housed in a housing having a chamber with two oriented grommets that prevent fluid flow through the chamber (other than through the needle assembly) both when the needle assembly is inserted through the chamber and when it is withdrawn. A beam spring blocks the chamber after the needle assembly is withdrawn so that the device cannot be reused.

16 Claims, 3 Drawing Sheets

DEVICE FOR PARACENTISIS AND THORACENTISIS

FIELD OF THE INVENTION

The present invention relates to the field of medical devices and, in particular, to a device useful for paracentesis and thoracentesis.

BACKGROUND

Body fluids may need to be withdrawn from a patient in the course of medical treatment. Two common medical procedures requiring fluid removal are thoracentesis and paracentesis.

In paracentesis, peritoneal fluid is aspirated from the abdomen. Typical patients have tense ascites resulting from liver disease and portal hypertension, which may cause discomfort, respiratory distress, and the formation and rupture of umbilical hernias. Paracentesis has been observed to provide quick and effective relief with few adverse side effects. Other treatment options, such as the use of diuretics, are available, but may not provide as effective relief as paracentesis. Additionally, many patients with ascites have renal impairment and cannot use the high doses of diuretics necessary to effectively treat the ascites. See "Large-Volume Paracentesis in Nonedematous Patients with Tense-Ascites: Its Effect on Intravascular Volume," Pinto et al., *Hepatology*, Vol.8, No. 2, pp. 207–210, 1988. Relatively large volumes of fluid, such as five liters, may be withdrawn from a patient during one paracentesis procedure.

Many existing devices are capable of performing paracentesis. At its simplest, a paracentesis device need only include a hollow needle with one end inserted into the patient and the other end attached to a negative pressure device, such as a syringe or vacuum bottle. However, more specialized devices have been developed to allow safer, more comfortable, and more sanitary paracentesis. These devices may allow for body fluid to be dispensed into at least two containers, so that one container may be filled with fluid for diagnostic purposes and the other container may be filled with waste fluid. Another development has been the use of Kuss or Verres type needle assemblies, where a blunt drainage needle is attached to a retractile sharp introducer needle. This reduces the likelihood of the sharp needle damaging internal tissue during paracentesis. A further development is to drain body fluid through a blunt-tipped catheter introduced by a sharp introducing needle, which allows the sharp needle to be removed from the patient after a relatively quick introduction process and avoids the prolonged presence of a sharp needle in the body of the patient.

Problems may arise when drainage is diverted from one container to another if the drainage system is not airtight. Air could contaminate a sample or enter the body of the patient and cause injury. Known devices that are meant to be airtight have tubes and multiple containers attached to the devices which make the devices cumbersome and somewhat difficult to insert into the patient. Also, known devices require manipulation of a manual valve, such as a stopcock to work effectively. If the stopcock is not set at the proper setting, the device may admit air into the patient or otherwise malfunction. Problems also may arise in devices which allow a needle assembly to be withdrawn. Air must be prevented from entering the patient when the fluid is withdrawn. Also, body fluid must be prevented from leaking out of the device through the space formerly occupied by the needle assembly.

Thoracentesis is a procedure similar to paracentesis, except that effusion fluid is withdrawn from the pleural region instead of the abdomen. Normally, the pleural space contains approximately 5 to 20 ml of fluid. The fluid is the result of the hydrostatic-onctotic pressure of the capillaries of the parietal pleura. The turnover of the fluid in the pleural space is normally quite rapid, so that 5 to 10 liters of fluid move through the pleural space each day. A disruption in the balance between the movement of fluid into the pleural space and the movement of fluid out of the pleural space may produce excessive fluid accumulation in the pleural space. Pleural effusion is particularly common in patients with disseminated breast cancer, lung cancer or lymphatic cancer and patients with congestive heart failure, but also occurs in patients with many other forms of malignancy.

Pleural effusion may cause dyspnea, coughing, and chest pain, which diminish a patient's quality of life. Although pleural effusion typically occurs toward the end of terminal malignancies, such as breast cancer, it occurs earlier in other diseases. Therefore, relieving the clinical manifestations of pleural effusion is of real and extended advantage to the patient. For example, non-breast cancer patients with pleural effusion have been known to survive for years. See "Pleural Effusion in Cancer Patients," Izbicki et al., *Cancer*, October 1975, p. 1511.

There are several treatments for pleural effusion. If the patient is asymptomatic and the effusion is known to be malignant or paramalignant, no treatment may be required. Pleurectomy and pleural abrasion are generally effective in obliterating the pleural space, thus controlling the malignant pleural effusion. However, pleurectomy is a major surgical procedure associated with substantial morbidity and some mortality. Chemotherapy is generally disappointing; however, it may produce good responses for patients with lymphoma, breast cancer, or small-cell carcinoma. Another approach is to surgically implant a chest tube. However, such a tube is painful to the patient, both when it is inserted and during the time that it remains in the pleural space. Improvements on the traditional chest tube are described in U.S. patent application Ser. No. 08/251,692, commonly owned with the present application.

Despite other treatment options, thoracentesis remains the most common approach to removing pleural fluid. However, thoracentesis poses the danger of causing pneumothorax, a collapsed lung. Pneumothorax can be caused directly by puncturing a lung with a needle assembly or catheter tip or indirectly by allowing air to enter the pleural space. Normally, the pleural space is at negative pressure relative to the atmosphere, which helps keep the lungs expanded. If the atmosphere is allowed to communicate with the pleural space, the pleural space may no longer be at negative pressure and pneumothorax may result.

Thoracentesis devices have been developed to reduce the risk of pneumothorax and other similar problems that may result from the procedure. In general, these devices incorporate similar protections as do paracentesis devices. For example, U.S. Pat. No. 4,447,235 by Clarke discloses a thoracentesis device with a catheter introduced by a removable needle assembly, with a valve that closes upon removal of the needle assembly. The purpose of the valve is to prevent air from entering the body of the patient. U.S. Pat. Nos. 4,784,156, 4,832,044, 4,840,184, and 4,844,087 by Garg disclose similar devices with a manual valve that may be closed after withdrawal of the needle assembly. However, none of the previous devices allow for a truly fail-safe operation, as various valves must be properly set by the operator when changing from one drain port to another or when withdrawing the introducing needle assembly from the patient. Also, care must be taken to avoid accidental withdrawal of the introducing needle assembly, as in the disclosed devices where the needle assembly is not firmly attached to the remainder of the device. Further, the disclosed valves that allow for catheter drainage after removal of an introducing needle assembly rely on a single contact point. Due to the possibly dire consequences of a valve failure, such valves may not produce acceptably safe thoracentesis.

A Verres-type needle assembly that may be used for thoracentesis is disclosed in U.S. Pat. No. 5,334,159 by Turkel. While this reduces the risk of pneumothorax due to lung puncture, the Turkel device does not improve the safety of thoracentesis when the introducing needle assembly is withdrawn or solve the problems associated with multiple drainage ports. Thus there is a need for a safer and more reliable device that may be used for paracentesis and thoracentesis.

A device for accomplishing broadly the same purposes of the present invention is described in U.S. patent application No. 08/583,813, now U.S. Pat. No. 5,725,906, issued Mar. 10, 1998. It is believed that the sealing arrangement among other features of the present invention may represent an improvement or an alternative to the device of said application.

The contents of each document referred to herein is hereby incorporated by reference, although it is noted that such documents are not admitted to be prior art and are only referenced as they may be helpful to an understanding and appreciation of the present invention.

SUMMARY

The present device for fluid removal from the body of a patient is characterized by the incorporation of several features to reduce the likelihood of damage to a patient during the procedure and to facilitate the fluid removal process. The primary components of the drainage device are a Verres-type needle assembly partially surrounded by a catheter, a housing through which the needle assembly and catheter pass, and a detachable handle to which the needle assembly is attached at its end opposite the end to be inserted into the patient.

The Verres-type introducing needle assembly includes a sharp outer needle and a blunt retractile inner needle. The inner needle is biased so that it projects ahead of the outer needle in the absence of an axial force on the inner needle. An axial force on the inner needle causes it to retract into the outer needle so that the sharp tip of the outer needle is exposed. Thus, pressing the device against the skin and dense outer tissue of a patient causes the sharp needle to become exposed and allows the needle assembly to cut through the skin and dense outer tissue and enter the body of the patient. When the needle assembly tip enters the fluid pool to be drained, however, there is no axial force on the inner needle and it extends from the outer needle. Once the Verres needle assembly is in the fluid pool, the sharp needle is buffered by the blunt needle and is less likely to cut into a patient's sensitive inner tissue. The device operator is made aware of whether the inner needle is projected ahead of the outer needle or recessed into the outer needle by means of an indicator that attaches to the end of the inner needle opposite the end that is inserted into the patient, and thus the operator may determine whether the needle tip has entered the fluid pool.

Fluid may be withdrawn through the Verres needle assembly through a drainage port on the device fitted with a Luer lock by applying negative pressure at the Luer lock. After the operator has withdrawn a quantity of fluid through the Verres needle assembly and is satisfied that the device is properly positioned, the Verres needle assembly may be withdrawn and further fluid may be withdrawn through the catheter. This allows for safer fluid withdrawal, since the sharp-tipped inner needle is removed from the body of the patient and for faster fluid withdrawal, since the catheter has a larger diameter than the Verres needle assembly. The needle assembly is withdrawn from the device by detaching the handle to which the Verres needle assembly is attached from the remainder of the device. A locking feature joining the handle to the housing ensures that the Verres needle assembly will not be inadvertently withdrawn.

Withdrawing an introducing needle from a fluid removal device is a critical stage in the fluid removal process because of the possibility of air entering the patient through the space formerly occupied by the needle assembly. Also, it is possible that fluid may leak out of the device through the same space. The present invention prevents both of these potential hazards by means of an automatic sealing valve that seals the space through which the needle assembly passes. In a preferred embodiment, the seal is formed by two grommets that surround the needle assembly within the housing and seal the housing both when the needle assembly is within the housing and when it is withdrawn. The grommets have slits though which the needle assembly passes that are self-sealing when the needle assembly is withdrawn. The grommets are oriented, and one grommet is located proximal to another distal grommet. The distal grommet is oriented in the distal direction, and so is particularly effective at blocking fluid flow from the patient. The proximal grommet is oriented in the proximal direction, and so is particularly effective at blocking atmospheric pressure from communicating with the patient.

The housing also contains a means for preventing the needle assembly from being reinserted into the housing once it has been withdrawn. Preferably, the means is a beam spring that is biased by the needle assembly when the needle assembly extends through the housing. The beam spring releases to occupy the needle assembly path after the needle assembly is withdrawn, and thus prevents the withdrawn needle assembly from being reinserted.

After the needle assembly is withdrawn, fluid may be withdrawn through the catheter through a second drainage port fitted with a Luer lock by attaching a negative-pressure device to the drainage port. The second port is blocked by the needle assembly until the needle assembly is removed from the device. Preferably, a sealing valve prevents the flow of air or fluid through the second port until a male Luer fitting is attached, coupled to a negative pressure device. This sealing valve allows the negative-pressure device to be attached to the second drainage port at any stage of the fluid withdrawal process. This is advantageous, as it may be easier to first insert the device into the patient without any attachments to the second drainage port, so that the device is more maneuverable. The valve also requires no manual adjustment.

The device may be inexpensively manufactured and is designed to be disposed of after one use. The Verres needle assembly is preferably made of metal, such as stainless steel. The catheter may be made of metal or plastic or other suitable material, plastic being somewhat softer than metal and hence providing additional safety for thoracentesis. The device housing and handle are made of rigid plastic, such as ABS plastic. The device housing may be made of several parts which are joined together after the internal components are placed in the housing. It should be understood that not all of the features described need be incorporated into a given device, and that the scope of the invention is defined by the claims and their legal equivalents.

DETAILED DESCRIPTION

Figure 1:
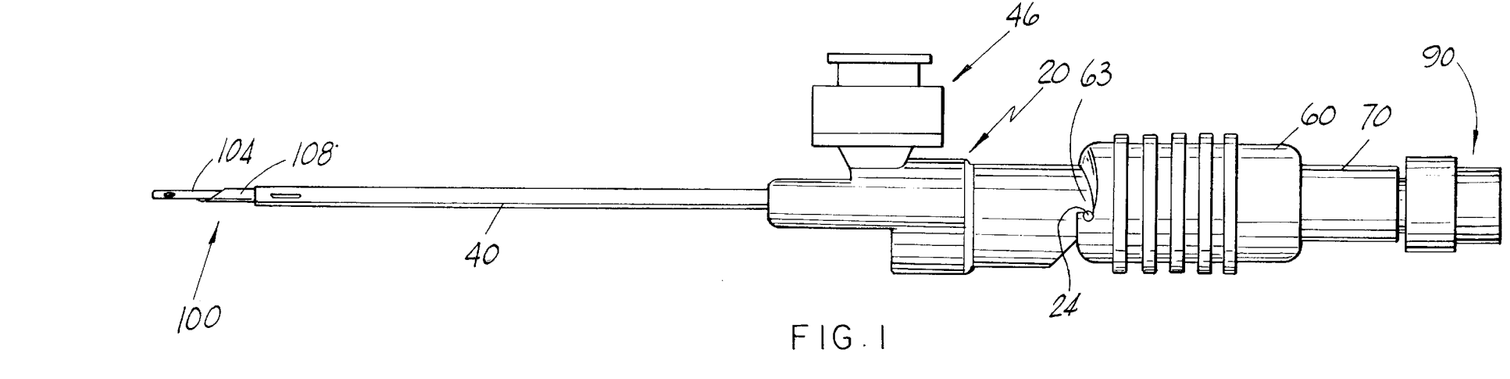
FIG. 1 shows a side view of an embodiment of the present invention.
Figure 2:
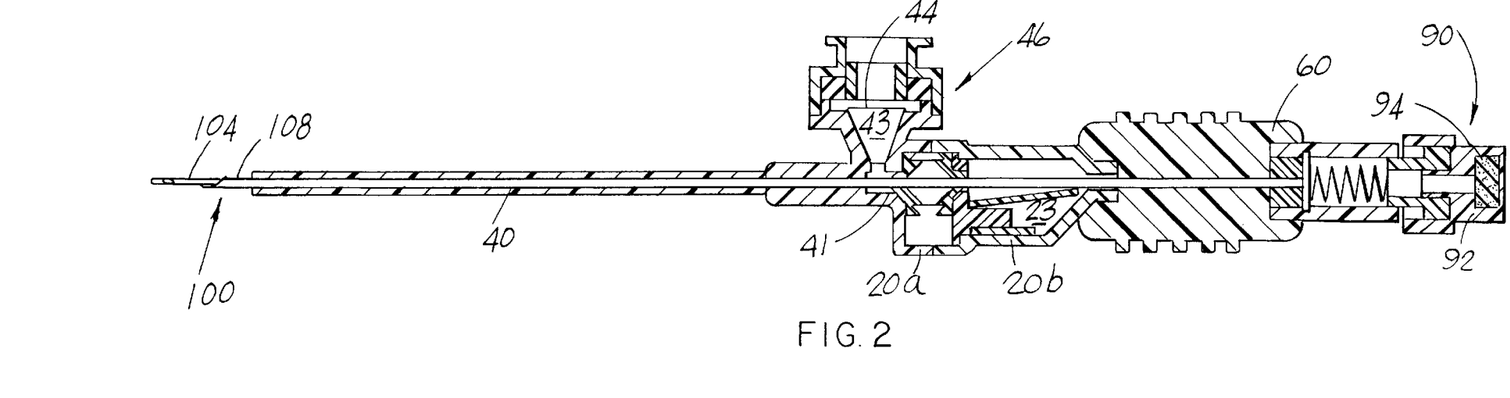
FIG. 2 shows a side sectional view of an embodiment of the present invention.

As best seen in FIGS. 1 and 2, a paracentesis and thoracentesis device 10 includes a housing 20 with a drainage cannula 40 extending from the distal end of the housing 20. The housing is most preferably formed of at least two components, such as distal housing component 20A and proximal housing component 20B, to facilitate manufacture. A transverse opening (side drainage port) 43 near the proximal end of the cannula 40 leads through a valve (sealing diaphragm) 44 to a transverse Luer lock 46 in the housing 20. The proximal end of the cannula 40 joins an interior cavity 23 in the housing 20 at a cannula opening 41. The cross section of the interior cavity 23 is larger than the that of the cannula 40; the interior cavity 23 extends proximally until its cross sectional diameter is reduced at its proximal end to form a proximal restriction 25. A primarily opaque detachable handle 60 attaches concentrically around the proximal end of the housing 20, and a transparent indicator housing 70 is situated so that a distal portion fits concentrically into the handle and a proximal portion extends proximal to the handle 60. The proximal end of the indicator housing 70 houses a proximal Luer lock 90. Both the handle 60 and the indicator 70 are hollow so that the proximal restriction 25 continues from the interior cavity 23 through a hole through the handle 60 and the indicator 70 to a proximal Luer lock 90. The Luer lock 90 preferably includes a venting cap 92 sealed by a vent plug 92. The vent plug 94 is preferably formed of a polyethylene based material (or the like) that is gas permeable and liquid impermeable.

Figure 3:
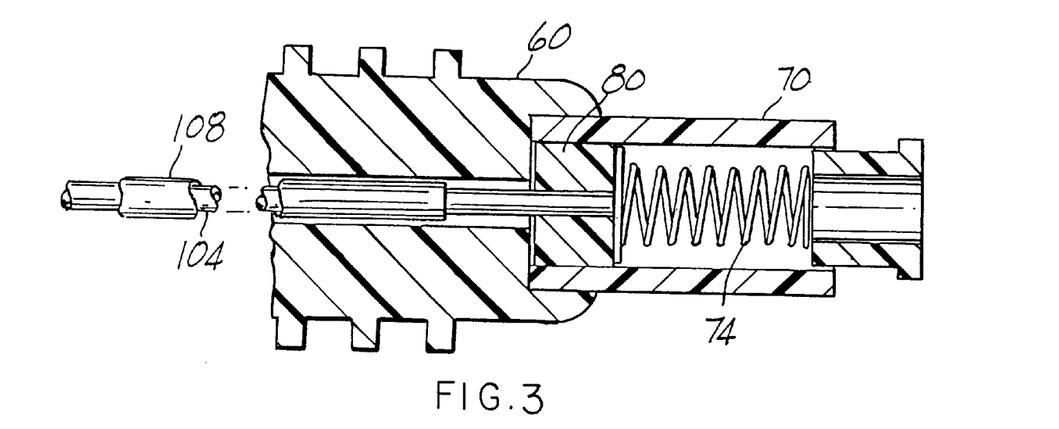
FIG. 3 shows a detailed sectional view of the needle assembly position indicator of the present invention when the inner needle assembly protrudes from the sharp outer needle assembly.
Figure 4:
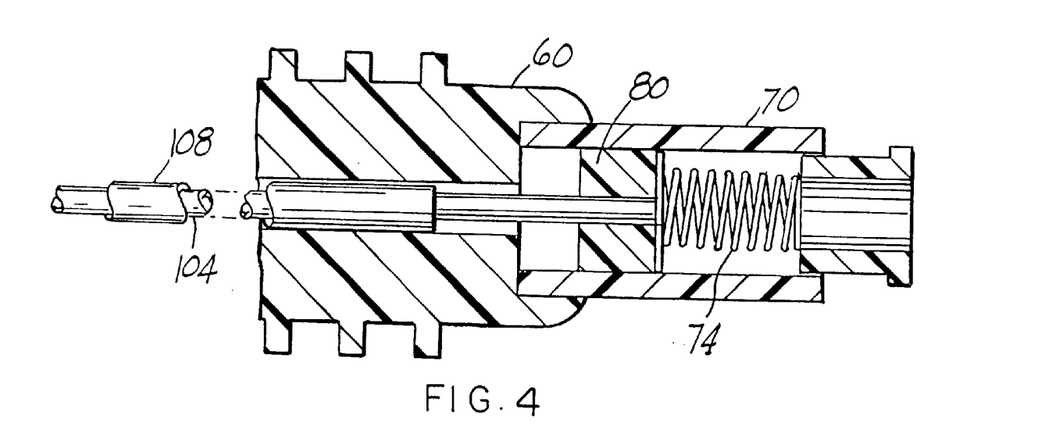
FIG. 4 shows the view of FIG. 3 when the inner needle assembly is recessed into the outer needle assembly, exposing the sharp outer needle assembly.

A Verres needle assembly 100 attaches to the handle 60 and extends through the proximal restriction 25, the interior cavity 23, and the cannula 40 and terminates distal to the cannula 40. The Verres needle assembly 100 includes an inner needle 104 with a blunt distal end and an outer needle 108 with a sharp distal end that fits concentrically around the inner needle 104. The outer needle 108 is firmly attached to the handle 60, such as by a gluing the two together. The inner needle 104 extends proximally to the outer needle 108. The inner needle 104 and outer needle 108 are slidably attached to each other, with the inner needle 104 biased by an indicator spring 74 so that, in the absence of a force to compress the spring 74, the inner needle projects distal to the outer needle 108 (see FIG. 3). When force is applied to the inner needle 104 in the proximal direction, the spring 74 compresses and the inner needle 104 recesses into the outer needle 108 (see FIG. 4). The biasing spring 74 is located on the interior surface of the indicator housing 70, with the distal end of the spring 74 terminated to the proximal end of inner needle 104. Both the catheter 40 and the inner needle 104 preferably contain one or more fenestrations in their sidewalls near their distal ends to facilitate fluid drainage.

An indicator 80 is fixed to the proximal end of the inner needle 104. The indicator 80 may be of any material, such as a colored piece of plastic, that is visible to the human eye. In a preferred embodiment, the indicator 80 is a colored plastic cylinder that fits concentrically around the inner needle 104. The dimensions of the inner needle 104 and the indicator 80 are such that when the inner needle 104 protrudes from the outer needle 108, neither the proximal end of the inner needle 104 nor the indicator 80 extend beyond the handle 60 (see FIG. 3). At this point, the indicator is not visible to the operator of the device 10. However, when the inner needle 104 recesses into the outer needle 108, the indicator 80 slides proximally along with the inner needle 104 so that the indicator 80 becomes visible through the transparent indicator housing 70 (see FIG. 4).

In its initial position, the handle 60, and hence the Verres needle assembly 100, is fixed in relation to the housing 20. A tab 24 protrudes from the housing 20 and fits into a tangential slot 63 on the handle 60 to fix the handle 60 in an initial position. The handle 60 may be rotated around the housing 20 so that the tab 24 is removed from the slot 63. Once the tab 24 is removed from the slot 63, the handle 60 may withdrawn proximally from the housing 20. As the Verres needle assembly 100 is attached to the handle 60, the Verres needle assembly 100 may be proximally removed from the housing 20 by sliding the handle 60 proximally from the housing 20.

Figure 5:
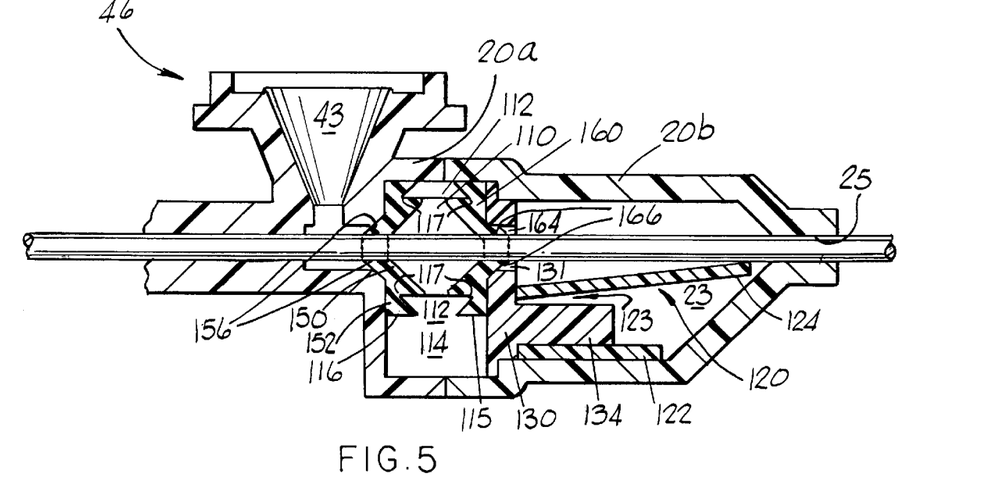
FIG. 5 shows a detailed sectional view of the interior chamber having means for preventing the reuse of the needle assembly before the introducing needle assembly has been withdrawn.
Figure 6:
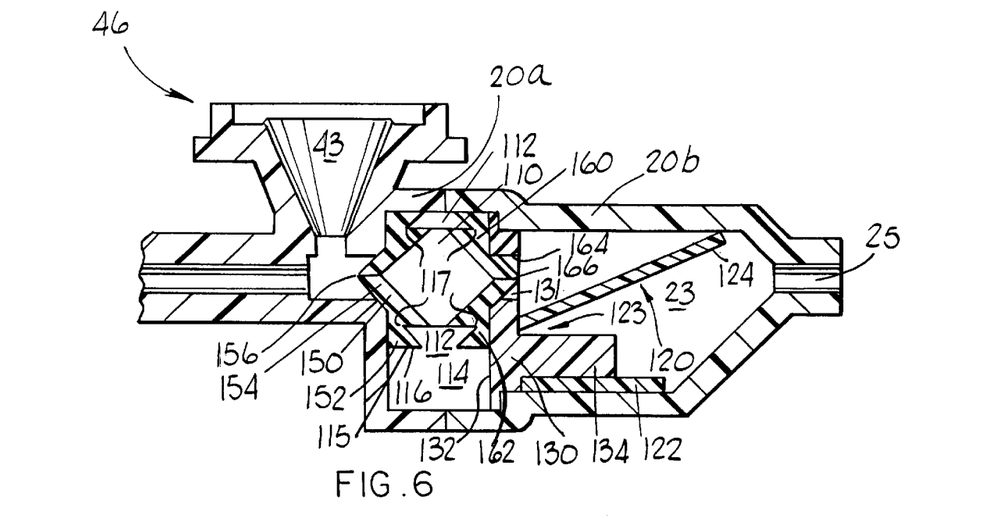
FIG. 6 shows the sectional view of FIG. 5 after the needle assembly has been withdrawn.

With reference to FIGS. 5 and 6, the interior cavity 23 houses a number of elements that serve two primary functions. The first function is a sealing function, so that no fluids or gases may leak through the cavity 23. In particular, fluid is prevented from leaking from the proximal end of the device 10 to the distal end, and atmospheric pressure is prevented from passing from the distal end of the device to the proximal end. The second function is a needle-blocking function, so that after the Verres needle assembly 100 is withdrawn from the device 10 the needle assembly cannot be reinserted. This ensures that the device 10 cannot be reused, which could be potentially dangerous to a patient. A preferred structure is first described, and then the unique suitability of the structure to perform the above functions is explained.

The proximal portion of the cavity 23 houses a seal collar 110. The seal collar has an annular component 112 defining an aperture within the annular component through which the Verres needle assembly passes. The aperture has a somewhat greater cross-section than the cross-section of the Verres needle assembly, as explained below. The annular component 112 sits atop a grommet bearing portion 114. The grommet bearing portion 114 has a proximal grommet lip 115 and a distal grommet lip 116. Each lip 115 and 116 is shaped to support a grommet in that lip. The lips 115, 116 extend axially for a distance to support a portion of their respective grommets. Preferably, the seal collar annular portion 112 is chamfered (or otherwise shaped), so that the interface between the annular portion 112 and the lips 115, 116 define a notch 117 along the length of each lip 115, 116 that exerts a compressive force on the grommet. Another notch 117 is formed by the chamfered annular portion 112 and the housing 20.

A seal plate 130 is positioned distal to the seal collar 110. The seal plate 130 spans the entire cross-section of the cavity 23. The seal plate 130 has an aperture 131 that aligns with the seal collar aperture so that the Verres needle assembly can pass through the seal plate 130. The seal plate 130 has a flush proximal face 132 that contacts the grommet bearing portion 114 of the seal collar 110. The proximal grommet lip 115 extends somewhat distal to the seal collar annular portion 112, so that the seal plate 130 is spaced away from the seal collar annular portion 112 in order to provide a grommet-bearing space. The seal plate 130 also includes a distally extending post 134, the purpose of which is explained below.

A distal grommet 150 and a proximal grommet 160, each of silicone or similar elastomeric material, are disposed within and across the cavity 23 to effectively seal the cavity 23. The distal grommet 150 is compressed between the distal housing portion housing 20A and the seal collar 110. The proximal grommet 160 is compressed between the proximal housing portion 20B, the seal collar 110, and the seal plate 130. Each grommet 150, 160 is generally of the "duck-bill" type, which means that they have an opening or slit near the grommet center (after the needle is inserted through the grommet) and are oriented as explained below. The orientation of the duck-bill grommets is such that fluid pressure on the narrowed side of the grommet compresses the grommet opening so that no fluid can flow through the grommet.

When the Verres needle assembly 100 extends through the cavity 23, the elastomeric grommets 150, 160 form fit around the needle assembly 100 so that no fluid or gas can penetrate the barriers formed by the grommets and the needle assembly. Most preferably, the grommet 150, 160 openings are formed by inserting the needle assembly 100 through the otherwise solid grommets. This ensures that each opening is no larger than necessary to accommodate the needle assembly 100, and also ensures that the needle and grommets 150, 160 are properly aligned. Alternatively, the grommets could be formed with openings therein, and the needle could be inserted through such grommet openings.

When the Verres needle assembly is retracted from the cavity 23, the grommets compress to close their openings, so that they each form a fluid tight barrier (it being understood that a "fluid tight barrier" as used herein refers to both liquids and gases at pressures in the range of fluids being transferred to or from a human or similar body in normal atmospheric conditions). Referring now specifically to the distal grommet 150, a central portion 154 extends more distal than an exterior portion 152 of the grommet, so that the grommet may be said to be oriented toward the distal direction. The central portion 154 terminates in a flat section 156. This is in contradistinction to a pointed section, which would be present if the central portion 154 were not truncated at the flat section 156. It has been discovered that the inclusion of the flat section 156 reduces excessive mass that would otherwise be present at the central portion 154. This allows the grommet 150 to seal more effectively than would otherwise be the case, as the excess mass would otherwise inhibit the closure of the opening in the grommet.

The orientation of the grommet 150 allows for a stronger seal to be formed to prevent fluid to flow in one direction compared to the other. The distal grommet 150 is oriented such that it is more difficult for fluid to flow from the distal direction than from the proximal direction. This is desirable, as the primary purpose of the distal grommet is to prevent fluid from leaking from the body of the patient into the central cavity 23. The distal grommet is particularly effective because of its shape and because of the tight fit achieved by the combination of the housing and the sealing collar 110.

Referring now specifically to the proximal grommet 160, a central portion 164 extends more proximal than an exterior portion 162 of the grommet, so that the grommet may be said to be oriented toward the proximal direction. The central portion 164 terminates in a flat section 166. This has the same advantages as described above in connection with the distal grommet 150, in terms of providing a stronger sealing force than would otherwise be the case.

The proximal grommet 160 may said to be oriented toward the proximal direction, and fluid and gases are more strongly prevented from flowing in the proximal direction than in the distal direction. This is desirable, as the primary purpose of the proximal grommet 160 is to prevent atmospheric pressure from outside of the device to pass through the cavity 23 and communicate with the interior of the patient. The configuration of the proximal grommet 160 is particularly effective in providing a sealing force, because of the configuration of the grommet and the tight fit between the sealing collar 110 and the sealing plate 130.

It should be appreciated that the seal formed by the inclusion of the two grommets 150, 160 is particularly effective because of the closed interior space formed within the cavity between the two grommets. The quantity of air occupying this interior space must be at least partially evacuated in order for fluid to flow between the grommets. Since the interior space is sealed, it requires effort to evacuate the air, and this additional effort strengthens the seal formed by the grommets.

The reuse of the device 10 is prevented by the action of a spring 120, which is a means for preventing the reinsertion of the needle assembly after it is been withdrawn from the chamber 23. The spring 120 has a base portion 122 and a beam portion 124 hingedly connected to the base portion. The base portion is rounded to mate flushly with the housing 20 and has an aperture 123 so that the spring 120 can be mounted on the seal collar post 134. This ensures that the device is correctly assembled and that a tight fit is achieved amongst the components. The unbiased tension of the spring 120 is such that the spring beam portion 124 obstructs the seal plate aperture 131 (see FIG. 5A). If the withdrawn needle 100 (or any other needle or similar object) were attempted to be reinserted through the chamber 23, the needle assembly would contact the spring beam portion 124, and so the attempt would be unsuccessful. Stated another way, the beam portion 124 extends a distance in a direction along the needle axis and another distance in a direction transverse to the needle axis in the biased position; when the beam portion is unbiased, it extends farther in the transverse direction so that it obstructs the needle path.

The beam portion 124 can be biased by the Verres needle 100 so that the needle assembly passes through the seal plate aperture 131 (as shown in FIG. 5). The biasing is accomplished in the manufacturing process, such as by inserting the needle 100 through the chamber from the distal end, thereby pushing the beam portion 124 down (as shown in the figures, not as an absolute direction) or by holding the beam portion 124 down in some manner. After the Verres needle 100 is withdrawn, the beam portion is no longer biased, and hence obstructs the aperture 131 as described above.

The operation of the device 10 to withdraw fluid from a patient may now be described. To perform thoracentesis, for example, the Verres needle assembly 100 is introduced into the pleural space of a patient. Before the Verres needle assembly 100 is positioned against the skin of a patient, the inner needle 104 projects distal to the outer needle 108. As the device 10 is pressed against the skin, pressure on the inner needle 104 causes the indicator spring 74 to compress and the inner needle 104 recesses into the outer needle 108 until the outer needle 108 is adjacent the skin of the patient. Further pressure on the device 10 causes the outer needle 108 to puncture the skin and dense outer tissue of the patient and to enter the patient's pleural cavity. While the outer needle 108 is cutting through tissue, axial pressure on the distal tip of the inner needle 104 keeps the inner needle recessed into the outer needle 108. Once the Verres needle assembly 100 enters the pleural cavity, the pressure on the distal tip of the Verres needle assembly 100 is removed and the indicator spring 74 decompresses and projects the inner needle 104 distal to the outer needle 108. The operator of the device 10 is made aware of the point where the Verres needle assembly 100 has entered the pleural cavity by the position of the indicator 80; the indicator 80 will not be visible through the indicator housing 70 when the Verres needle assembly 100 is in the patient's pleural cavity.

It should be apparent that the use of a Verres needle assembly 100 serves to protect the patient's sensitive inner tissue, particularly the lungs, from inadvertent puncture by the sharp outer needle 108. Once the operator of the device 10 detects that the Verres needle assembly 100 is in the pleural cavity, the operator may stop the distal motion of the Verres needle assembly 100. Further inadvertent distal motion, by either the device 10 operator or the patient, is relatively harmless until the blunt inner needle 104 contacts sensitive tissue and further distal motion causes the inner needle 104 to fully recess into the sharp outer needle 108. Harm to a patient may occur if the patient moves in the proximal direction, as well as when the operator of the device 10 moves the device 10 in the distal direction. Such movement is a particular problem in thoracentesis, since a patient's lungs move proximally and distally as the patient inhales and exhales. So while the Verres needle assembly 100 affords some protection against pneumothorax or other tissue harm, it is by no means fail-safe.

Fluid may be withdrawn through the Verres needle assembly 100 through the proximal Luer lock 90 attached to the indicator 70 by means of a negative pressure device (not shown), such as a syringe, attached to the proximal Luer lock 90. The negative pressure device may be attached to the Luer lock 90 before the device 10 is introduced into the body of the patient so that no air enters the body of the patient through the device 10. It is possible that body pressure and capillary action may cause body fluid to flow into the annular space separating the drainage cannula 40 and the outer needle 108. However, the distal grommet 150 placed around the sharp needle 108 distal to the side drainage port 43 blocks the flow of fluid beyond the distal grommet.

After the operator of the device 10 determines that the fluid is flowing properly and desires that more fluid be withdrawn from the patient, the drainage may be completed through the catheter 40 and the side drainage port 43, instead of through the Verres needle assembly 100 and the proximal Luer lock 90. The transition is initiated by the operator withdrawing the Verres needle assembly 100 from the patient while keeping the housing 20 fixed. This is accomplished by rotating the handle 60 so that the tab 24 on the housing 20 is no longer in the tangential slot 63 of the handle 60, then pulling the handle 60 in the proximal direction while maintaining the position of the housing 20. Body fluid may then flow directly through the drainage cannula 40. As the Verres needle 100 is withdrawn proximal to the chamber 23, the chamber is effectively sealed by the proximal and distal grommets 150, 160 as explained in detail above. Further, the spring beam portion 124 blocks the interior cavity 23, so that the needle assembly cannot be reinserted and so the device cannot be reused.

After removal of the Verres needle assembly 100, drainage is accomplished directly through the drainage cannula 40 and the locking Luer fitting 46 of the side drain port 43. Removal of the Verres needle assembly 100 from the body of the patient is desirable to eliminate the possibility of the sharp outer needle 108 from severing tissue, particularly the lungs, of the patient. While the blunt inner needle 104 of the Verres needle assembly 100 reduces the danger posed by the sharp outer needle 108, additional safety is achieved by removing the Verres needle assembly 100 entirely from the patient. Also, the diameter of the drainage cannula 40 is greater than the diameter of the blunt needle 104 of the Verres needle assembly 100, so that fluid may be withdrawn more rapidly. The two drainage ports 43 and 90 also allow fluid to be collected into separate containers. This may be useful as the device 10 operator may wish to withdraw a diagnostic sample through the proximal Luer lock 90 and withdraw the remaining fluid through the side Luer lock 46 for disposal.

As with the proximal Luer lock 90, any negative-pressure device and storage container with a Luer fitting may be attached to the side drain port 43. Further, the side drain port 43 provides an airtight seal until a device fitted with Luer lock is attached to the Luer lock 46 of the drain port. This is desirable as air entering the device 10 through the drain port 43 could then enter the body of the patient and produce pneumothorax, as explained above. In a preferred embodiment, the seal is accomplished via the valve 44. Prior art body fluid drainage devices are equipped with valves, such as stopcocks, which require the operator to manually adjust the valve when changing the fluid flow from one drainage channel to another. A manual stopcock may endanger the patient if it is inadvertently set to the wrong setting. For example, the operator could bump the stopcock setting so that the stopcock would allow the entry of air through the device into the body of the patient. A partial solution to that danger has been to terminate the stopcock openings with sealed components before the drainage device is inserted into a patient. However, a drainage device so equipped must be bulky and the operator must bear in mind the relative positions of the various components of the device, which may make insertion of the device difficult. In the present invention, the device 10 is preferably inserted with no attachment to the side drainage port 43. There is no danger of accidentally opening the Luer lock 46 on the side drainage port 43, and no drainage container need be attached to the side drainage port until after the device 10 is inserted into the patient.

What is claimed is:

1. A fluid withdrawal device, comprising:
   a retractable needle assembly for insertion into a body;
   a housing that contains at least a portion of the needle assembly, the housing including a chamber having a distal end and a proximal end;
   a distal grommet disposed within and across the chamber, the distal grommet having an opening so that the distal grommet form fits around the needle assembly, so that the distal grommet forms a substantially fluid tight barrier across the chamber;

a proximal grommet disposed within and across the chamber at a position proximal to the distal grommet, the proximal grommet having an opening so that the proximal grommet form fits around the needle assembly, so that the proximal grommet forms another substantially fluid tight barrier across the chamber;

the grommets being elastomeric so that they compress to close their openings when the needle assembly is retracted form the chamber, so that each grommet maintains the substantially fluid tight barrier across the chamber;

wherein the distal grommet is oriented in the distal direction, so that the distal grommet resists fluid flow from the distal direction more than from the proximal directions, and the proximal grommet is oriented in the proximal direction, so that the proximal grommet resists fluid flow from the proximal direction more than from the distal direction;

wherein the distal grommet is oriented in the distal direction by having a central portion that extends further in the distal direction than an exterior portion; and the proximal grommet is oriented in the proximal direction by having a central portion that extends further in the proximal direction than an exterior portion;

further comprising a seal collar having an aperture through which the needle assembly passes, the seal collar having a distal grommet lip and a proximal grommet lip, each extending axially for a distance to support the distal and proximal grommets.

2. The fluid withdrawal device of claim 1, wherein a notch is formed between the seal collar annular portion and each of the seal collar grommet lips, whereby a compressive force is exerted on said grommets.

3. The fluid withdrawal device of claim 2, further comprising a seal plate positioned distal to the seal collar, the seal plate having an aperture aligned with the seal collar aperture through which the needle assembly passes; the distal grommet being compressed between the housing and the seal collar, and the proximal grommet being compressed between the housing, the seal collar, and the seal plate.

4. The fluid withdrawal device of claim 3, wherein a means for preventing the reinsertion of the needle assembly after the needle assembly has been withdrawn from the chamber is mounted to the seal plate.

5. The fluid withdrawal device of claim 4, wherein the means for preventing the reinsertion of the needle assembly includes a spring.

6. The fluid withdrawal device of claim 5, wherein the spring has a beam spring portion.

7. The fluid withdrawal device of claim 6, wherein the beam spring portion is biased by the needle assembly when the needle assembly extends through the chamber, and the beam spring portion obstructs the path of the needle assembly if the needle assembly is attempted to be reinserted so that the needle assembly contacts the spring and is thereby prevented from being reinserted.

8. The fluid withdrawal device of claim 7, wherein the spring has a base portion and the beam spring portion is hingedly connected to the base spring portion.

9. The fluid withdrawal device of claim 8, wherein the base portion is mounted to the seal plate.

10. The fluid withdrawal device of claim 9, wherein the base portion has an aperture, and the seal plate has a post inserted through the aperture.

11. A fluid withdrawal device, comprising:
a retractable needle for insertion into a body;
a housing that contains a least a portion of the needle assembly;
a spring having a beam spring portion disposed within said chamber, the beam spring portion being biased by the needle assembly when the needle assembly is inserted through the chamber, the beam spring having an unbiased position that blocks the needle assembly after the needle assembly has been retracted from the chamber so that the needle assembly cannot be reinserted through the chamber.

12. The fluid withdrawal device of claim 11, wherein the beam spring portion extends in a direction along a needle axis and a direction transverse to the needle axis when the beam spring portion is biased by the needle assembly, and the beam spring portion extends further in the direction transverse to the needle axis after the needle assembly is withdrawn from the chamber.

13. The fluid withdrawal device of claim 12, wherein the spring has a base portion hingedly connected to the beam spring portion.

14. The fluid withdrawal device of claim 13, further comprising a seal plate having a post, and the base spring portion has an aperture through which the seal plate post is inserted.

15. A fluid withdrawal device, comprising:
a retractable needle assembly for insertion into a body;
a housing that contains at least a portion of the needle assembly, the housing including a chamber having a distal end and a proximal end;
a distal grommet disposed within and across the chamber, the distal grommet having an opening so that the distal grommet form fits around the needle assembly, so that the distal grommet forms a substantially fluid tight barrier across the chamber;
a proximal grommet disposed within and across the chamber at a position proximal to the distal grommet, the proximal grommet having an opening so that the proximal grommet form fits around the needle assembly, so that the proximal grommet forms another, substantially fluid tight barrier across the chamber;
the grommets being elastomeric so that they compress to close their openings when the needle assembly is retracted form the chamber, so that each grommet maintains the substantially fluid tight barrier across the chamber;
wherein the distal grommet is oriented in the distal direction, so that the distal grommet resists fluid flow from the distal direction more than from the proximal directions, and the proximal grommet is oriented in the proximal direction, so that the proximal grommet resists fluid flow from the proximal direction more than from the distal direction;
wherein the openings of the grommets are formed by insertion of the needle assembly through the grommets.

16. A fluid withdrawal device, comprising:
a retractable needle assembly for insertion into a body;
a housing that contains at least a portion of the needle assembly, the housing including a chamber having a distal end and a proximal end;
a distal grommet disposed within and across the chamber, the distal grommet having an opening so that the distal grommet form fits around the needle assembly, so that the distal grommet forms a substantially fluid tight barrier across the chamber;
a proximal grommet disposed within and across the chamber at a position proximal to the distal grommet, the proximal grommet having an opening so that the proximal grommet form fits around the needle assembly, so that the proximal grommet forms another substantially fluid tight barrier across the chamber;

the grommets being elastomeric so that they compress to close their openings when the needle assembly is retracted form the chamber, so that each grommet maintains the substantially fluid tight barrier across the chamber;

wherein the distal grommet is oriented in the distal direction, so that the distal grommet resists fluid flow from the distal direction more than from the proximal directions, and the proximal grommet is oriented in the proximal direction, so that the proximal grommet resists fluid flow from the proximal direction more than from the distal direction;

wherein the grommets are symmetrical in cross section.

* * * * *